United States Patent [19]
Dolle, III et al.

[11] Patent Number: 5,986,102
[45] Date of Patent: Nov. 16, 1999

[54] HYDROXYPROPYLAMIDE PEPTIDOMIMETICS AS INHIBITORS OF ASPARTYL PROTEASES

[75] Inventors: Roland Ellwood Dolle, III, King of Prussia, Pa.; Cullen Lee Cavallaro, Hightstown; Timothee Felix Herpin, Princeton, both of N.J.

[73] Assignee: Pharmacopeia, Inc., Princeton, N.J.

[21] Appl. No.: 09/069,380

[22] Filed: Apr. 29, 1998

[51] Int. Cl.$^6$ .................................................. C07D 295/14
[52] U.S. Cl. ........................................... 548/164; 544/391
[58] Field of Search ..................... 544/168, 391

[56] References Cited

FOREIGN PATENT DOCUMENTS 0 209 897 A2   7/1986   European Pat. Off. .

OTHER PUBLICATIONS

Atsuumi, Shugo et al. "Renin Inhibitors. III. Synthesis and Structure–Activity Relationships of Transition–State Inhibitors Containing Dihydroxyethylene Isotere at the P1–P1 Site", Chem. Pharm. Bull. 42(2) 306–313 (1994).

Cavallaro et al, Chemical Abstracts, vol. 130, No. 324763, 1999.

*Primary Examiner*—Robert W. Ramsuer
*Attorney, Agent, or Firm*—Heslin & Rothenberg, P.C.

[57] ABSTRACT

Compounds of Formula I

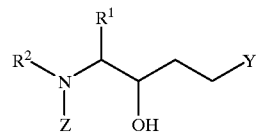

are disclosed as inhibitors having activity against the aspartyl proteases, plasmepsin and cathsepsin D. The compounds are useful for treatment of diseases such as malaria and Alzheimer's disease. In preferred compounds of Formula I, Y is a heterocycle, amide, sulfonamide or carbamate and Z is an acyl or a functionalized acyl. Intermediates in the solid phase synthesis of compounds of Formula I, in which compounds are attached to a solid phase support, are also disclosed.

10 Claims, No Drawings

HYDROXYPROPYLAMIDE PEPTIDOMIMETICS AS INHIBITORS OF ASPARTYL PROTEASES

CROSS-REFERENCE

Combinatorial Amide Alcohol Libraries, U.S. Ser. No. 08/843,214, filed Apr. 14, 1997, is incorporated herein by reference.

All patents and other references cited herein are incorporated by reference.

FIELD OF THE INVENTION

The present invention relates to peptidomimetic analogs (hydroxypropyl amides) that display inhibitory activity against the aspartyl proteases, plasmepsin and cathepsin D.

BACKGROUND OF THE INVENTION

The malaria parasite avidly consumes the host hemoglobin as a source of nutrients. Plasmepsin I and II are proteases from *Plasimodium falciparum* that are required for the initial stages of hemoglobin digestion. The primary site of hydrolysis is in the α-chain of hemoglobin between Phe 33 and Leu 34; however other sites are substrates as well. It has been shown that a peptidomimetic inhibitor blocked plasmepsin, thus preventing hemoglobin degradation and resulting in death of the malaria parasite in culture (Francis, S. E., Gluzman, I. Y., Oksman, A., Knickerbocker, A., Mueller, R., Bryant, M. L,., Sherman, D. R., Russell, D. G. and Goldberg, D. E. (1994) *EMBO J.* 13, 306–317). Due to the increasing problem of resistance to known antimalarial therapies, new antimalarial therapies are desperately needed. Therefore, plasmepsin inhibition is an excellent target for antimalarial therapy.

Cathepsin D is a human protease in the endosomal-lysosomal pathway involved in lysosomal biogenesis and protein targeting. Cathepsin D may also be involved in antigen processing and presentation of peptide fragments. Therefore, cathepsin D displays broad substrate specificity but prefers hydrophobic residues on either side of the scissile bond. Cathepsin D has been implicated in a variety of diseases such as connective tissue disease, muscular dystrophy and breast cancer. Most recently, cathepsin D is believed to be γ-secretase, the protease which processes the β-amyloid precursor protein to generate the C-terminus of β-amyloid (Dreyer, R. N., Bausch, K. M., Fracasso, P., Hammond, L. J., Wunderlich, D., Wirak, D. O., Davis, G., Brini, C. M., Bucholz, T. M., Konig, G., Kamark, M. E., and Tamburini, P. P. (1994) *Eur. J. Biochem.*, 224, 265–271 and Ladror, U. S., Synder, S. W., Wang, G. T., Holzman, T. F., and Krafft, G. A. (1994) *J. Biol. Chem.*, 269, 18422–18428). β-Amyloid is the major component of plaques in the brains of Alzheimer's patients. Therefore, inhibitors of cathepsin D could be useful in treating various human diseases.

The present invention relates to hydroxypropyl amides and their inhibiting action against aspartyl proteases. In particular, the invention relates to the identification of inhibitors that display selective inhibitory activity against plasmepsin and cathepsin D. Although statine-containing peptides are known to inhibit aspartyl proteases (Shewale, J. G.; Takahashi, R.; Tang, J.; *Aspartic Proteinases and Their Inhibitors*, Kostka, V., Ed. Walter de Gruyter: Berlin, 1986; pp 101–116), few potent and selective inhibitors are known for plasmepsin (U.S. Pat. No. 5,734,054). The invention also relates to the solid phase synthesis of such agents.

SUMMARY OF THE INVENTION

In one aspect, the invention is directed to compounds of Formula I:

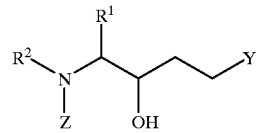

wherein:

$R^1$ is chosen from the group consisting of alkyl, —$(CH_2)_n$-cycloalkyl and aralkyl; where n=1–3;

$R^2$ is H or [S]—C(O)—L—, wherein [S] is a solid support and —L— is a linker;

Y is —OC(O)$NHR^3$ or —$NR^4R^5$, wherein $R^3$ is alkyl, aralkyl, aryl or aryloxyalkyl and $R^4$ and $R^5$ are independently selected from the group consisting of H, alkoxyalkyl, $R^3$, —$C(O)R^3$, —$SO_2R^3$,

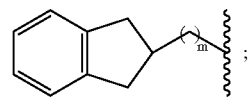

wherein m=0–3; or $R^4$ and $R^5$ together with the nitrogen atom to which they attach is

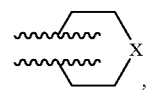

where X=$NR^6$ or O;

$R^6$ is chosen from the group consisting of H, $R^3$, —C(O)R and —$SO_2R^3$;

z is chosen from the group consisting of —$C(O)R^7$, —$C(O)CH(R^8)OC(O)NHR^3$ and —$C(O)CH(R^8)NHC(O)R^3$; wherein $R^7$ is chosen from the group consisting of alkyl, aralkyl, aryl, —$(CH_2)_m$-cycloalkyl, heteroaryl,

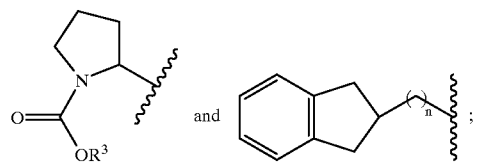

and $R^8$ is chosen from the group consisting of H, alkyl, aralkyl and —$(CH_2)_m$-cycloalkyl.

In another aspect, the invention is directed to a method for treating a condition by inhibiting the action of plasmepsin. Particularly, the invention is directed to a method for conducting antimalarial therapy in a human suffering from malaria, comprising administering a therapeutically effective amount of a compound of Formula I.

In an additional aspect, the invention is directed to a method for treating a condition by inhibiting the action of cathepsin D. The particular invention is directed to a method for treating Alzheimer's disease in a human, which comprises administering a therapeutically effective amount of a compound of Formula I.

Another aspect of the invention is the use of divinylbenzene-cross-linked, polyethyleneglycol-grafted polystyrene beads optionally functionalized with amino groups (e.g., TentaGel™ S NH$_2$, Rapp Polymere) as the solid supports for constructing compounds of Formula I.

DETAILED DESCRIPTION OF THE INVENTION

Abbreviations and Definitions

The following abbreviations and terms have the indicated meanings throughout:

Ac=Acetyl
BNB=4-bromomethyl-3-nitrobenzoic acid
BOC=t-butoxycarbonyl
BSA=bovine serum albumin
Bu=butyl
c-=cyclo
DABCYL=4-(4-dimethylaminophenylazo)benzoic acid
DBU=1,8-Diazabicyclo[5.4.0]undec-7-ene
DCM=Dichloromethane=methylene chloride=CH$_2$Cl$_2$
DIC=diisopropylcarbodiimide
DIEA=N,N-diisopropylethylamine
DMAP=4-(N,N-dimethylamino)pyridine
DMF=N,N-dimethylformamide
DMSO=Dimethyl sulfoxide
DVB=1,4-divinylbenzene
EDANS=5-[(2-aminoethyl)amino]naphthalenle-1-sulfonic acid
EI=eletron impact ionization
fab=fast atom bombardment
Fmoc=9-fluorenylmethoxycarbonyl
HOAc=acetic acid
HOBt=1-hydroxybenzotriazole
IBX=iodoxybenzoic acid
in vacuo=under vacuum
m-=meta
Me=methyl
NMO=N-methylmorpholinc oxide=4-methylmorpholine N-oxide
PEG=polyethylene glycol
Ph=phenyl
PfP=pentafluorophenol
r.t.=room temperature
sat'd=saturated
s-=secondary
t-=tertiary
TBS=tert-butyldimethylsilyl
TFA=trifluoroacetic acid
THF=tetrahydrofuran
TMOF=trimethyl orthoformate
TMS=trimethylsilyl
Tf=trifluoromethanesulfonyl
Tris=tris(hydroxymethyl)aminomethylene
Tween 20=polyoxyethylenesorbibtan monolaurate
UV=ultraviolet light "Alkoxy" means alkoxy groups of from 1 to 8 carbon atoms of a straight, branched or cyclic configuration and combinations thereof. Examples of alkoxy groups include: methoxy, ethoxy, propoxy, isopropoxy, cyclopropyloxy, cyclohexyloxy and the like.

"Alkyl" is intended to include linear or branched hydrocarbon structures and combinations thereof.

"Alkoxyalkyl" means an alkyl substituted with an alkoxy group. For example: methoxyethyl, isopropoxyethyl, ethoxymethyl and the like.

"Aralkyl" means an alkyl containing an aryl ring. For example: benzyl, phenethyl, 4-chlorobenzyl, diphenylethyl and the like.

"Aryl" is a 6-membered or 10-membered aromatic ring system where each of the rings is optionally substituted with 1–3 substituents selected from alkyl, halogen, hydroxy, alkoxy, aryloxy, haloalkyl, phenyl or heteroaryl; and wherein the phenyl is optionally substituted with 1–3 substituents selected from alkyl, halogen or alkoxy. Examples of aryl groups are phenyl and naphthyl.

"Aryloxy" means aphenoxy group where the phenyl ring is optionally substituted with 1 to 2 groups selected from halo, alkoxy or alkyl.

"Cycloalkyl" includes cycloalkyl groups of from 3 to 12 carbon atoms. Examples of "cycloalkyl" groups include: c-propyl, c-butyl, c-pentyl, c-hexyl, 2-methylcyclopropyl, norbornyl, adamantyl and the like.

"Haloalkyl" means one or more hydrogen atoms present in an alkyl group are replaced with a halogen atom, except for the methylene hydrogens adjacent to the oxygen atom. For example: 2-chlorocthyl and 2,2,2-trifluoroethyl.

"Halogen" includes F, Cl, Br and I, with F and Cl as the preferred groups.

"Heteroaryl" means a 5- or 6-membered heteroaromatic ring containing 1–3 heteroatoms selected from O, N and S; or a bicyclic 9- or 10-membered heteroaromatic ring system containing 1–4 heteroatoms selected from O, N and S; where the methine H atoms may be optionally substituted with alkyl, alkoxy or halogen. Examples of 5- to 10-membered aromatic heterocyclic rings include: imidazole, pyridine, indole, thiophene, benzopyranone, thiazole, furan, benzimidazole, quinoline, isoquinoline, quinoxaline, pyrimidine, pyrazine, tetrazole and pyrazole and the like.

"Heteroaralkyl" means an alkyl containing a heteroaryl ring. For example: pyridinylmethyl, pyrimidinylethyl and the like.

"Heterocyclyl" means a 5- or 6-membered heterocyclic ring containing 1–2 heteroatoms selected from O, N, and S; or a bicyclic 9- or 10-membered heterocyclic ring system containing 1–3 heteoatoms selected from O, N and S; where the methylene H atoms may be optionally substituted with alkyl, alkoxy or halogen. The 5- to 10-membered aromatic heterocyclic rings include rings, such as decahydroquinolinyl, morpholinyl, piperazinyl, piperidinyl, pyrrolidinyl, tetrahydrofuranyl, tetrahydropyranyl and tetrahydrothiophenyl.

"Lower Alkyl" means alkyl groups of from 1 to 12 carbon atoms. Examples of alkyl groups include alkyl groups such as methyl, ethyl, propyl, isopropyl, butyl, s- and t-butyl, pentyl, hexyl, octyl and the like.

"Therapeutically effective amount" refers to that amount of a compound of the invention which, when administered to a human in need thereof, is sufficient to effect treatment, as defined below, by inhibiting the action of plasmepsin I and II or cathepsin D. The amount of a compound of the invention which constitutes a "therapeutically effective amount" will vary depending on the compound, the condition and its severity, and the age of the human to be treated, but can be determined routinely by one of ordinary skill in the art having regard to his own knowledge and to this disclosure.

"Treating" or "treatment" as used herein covers the treatment of a condition in a human, by inhibiting the action of plasmepsin I and II or cathepsin D, and includes:

(i) preventing the condition from occurring in a human, in particular, when such human is predisposed to the condition but has not yet been diagnosed as having it;
(ii) inhibiting the condition, i.e., arresting its development; or
(iii) relieving the condition, i.e., causing regression of the condition.

Treatment involves inhibition of the protease actions of plasmepsin I and II or cathepsin D.

The material upon which the syntheses of the invention are performed are referred to as solid supports, beads and resins. These terms are intended to include: beads, pellets, disks, fibers, gels or particles such as cellulose beads, pore-glass beads, silica gels, polystyrene beads optionally cross-linked with divinylbenzene and optionally grafted with polyethylene glycol and optionally functionalized with amino, hydroxy, carboxy or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface and soluble supports such as low molecular weight non-cross-linked polystyrene.

Preferred Embodiments

The compounds of the present invention are represented by Formula I:

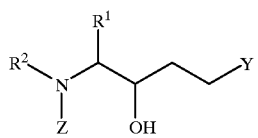

I wherein:
$R^1$ is chosen from the group consisting of alkyl, —$(CH_2)_n$-cycloalkyl and aralkyl;
where n=1–3;
$R^2$ is H or [S]—C(O)—L—, wherein [S] is a solid support and —L— is a linker;
Y is —OC(O)$NHR^3$ or —$NR^4R^5$, wherein $R^3$ is alkyl, aralkyl, aryl or aryloxyalkyl, and
$R^4$ and $R^5$ are independently selected from the group consisting of H, alkoxyalkyl, $R^3$, —C(O)$R^3$, —$SO_2R^3$,

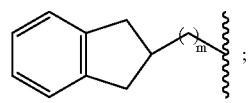

wherein m=0–3; or when $R^4$ and $R^5$ together with the nitrogen atom to which they attach is

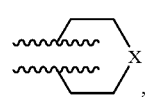

where X=$NR^6$ or O;
$R^6$ is chosen from the group consisting of H, $R^3$, —C(O)$R^3$ and —$SO_2R^3$;
Z is chosen from the group consisting of —C(O)$R^7$, —C(O)CH($R^8$)OC(O)$NHR^3$ and —C(O)CH($R^8$)NHC (O)$R^3$; wherein $R^7$ is chosen from the group consisting of alkyl, aralkyl, aryl, —$(CH_2)_m$-cycloalkyl, heteroaryl,

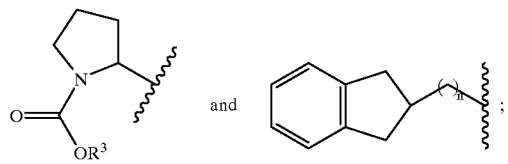

and $R^8$ is chosen from the group consisting of H, alkyl, aralkyl and —$(CH_2)_m$-cycloalkyl.

Preferred compounds of Formula I are those wherein —L— is

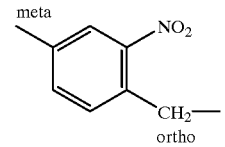

(a)

wherein the designated meta-position attaches to the carbonyl, (—C(O)—), that is attached to the solid support, [S] and the ortho-methylene attaches to the amide nitrogen of Formula I.

A preferred embodiment of the invention are compounds of Formula I wherein:
$R^2$ is H.

A preferred embodiment of the invention are compounds of Formula I wherein:
Y is —OC(O)$NHR^3$ wherein $R^3$ is aryl; and
Z is —C(O)$R^7$ wherein $R^7$ is aryl.

Another preferred embodiment of the invention are compounds of Formula I wherein:
Y is —OC(O)$NHR^3$ wherein $R^3$ is aryl; and
Z is —C(O)CH($R^8$)OC(O)$NHR^3$ or —C(O)CH($R^8$)NHC(O)$R^3$ wherein $R^8$ is alkyl.

A preferred embodiment of the invention are compounds of Formula I wherein:
Y is $NR^4R^5$; and
Z is —C(O)$R^7$.

Another preferred embodiment of the invention are compounds of Formula I wherein:
Y is —$NR^4R^5$ where $R^4$ is —C(O)$R^3$ and $R^5$ is alkyl, alkoxyalkyl or aralkyl; and
Z is —C(O)$R^7$ wherein $R^7$ is alkyl, aralkyl, aryl, —$(CH_2)_m$-cycloalkyl, heteroaryl or

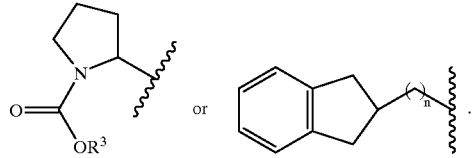

A further preferred embodiment of the invention are compounds of Formula I wherein:
Y is —$NR^4R^5$ where $R^4$ is —C(O)$R^3$ and $R^5$ is alkyl, alkoxyalkyl or aralkyl; and
Z is —C(O)$R^7$ wherein $R^7$ is aralkyl or aryl.

Yet a further preferred embodiment of the invention are compounds of Formula I wherein:

Y is —$NR^4R^5$ where $R^4$ is —$C(O)R^3$ and $R^5$ is alkyl, alkoxyalkyl or aralkyl; and Z is —$C(O)R^7$ where $R^7$ is alkyl, heteroalkyl or

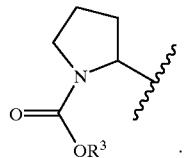

A preferred embodiment of the invention are compounds of Formula I wherein:

Y is —$NR^4R^5$ where $R^4$ is —$SO_2R^3$ and $R^5$ is alkyl, aralkyl, aryl or

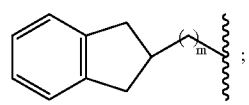

and

Z is —$C(O)R^7$ wherein $R^7$ is alkyl, aralkyl, aryl, —$(CH_2)_m$-cycloalkyl or

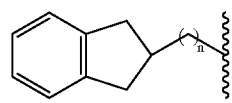

Another preferred embodiment of the invention are compounds of Formula I wherein:

Y is —$NR^4R^5$ where $R^4$ and $R^5$ together with the nitrogen atom to which they attach is

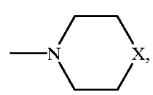

where $X=NR^6$ or O; and

Z is —$C(O)R^7$ wherein $R^7$ is alkyl, aralkyl, aryl or —$(CH_2)_m$-cycloalkyl.

A further preferred embodiment of the invention are compounds of Formula I wherein:

Y is —$NR^4R^5$ where $R^4$ and $R^5$ together with the nitrogen atom to which they attach is

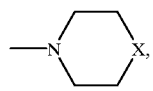

where $X=NR^6$ or O; and

Z is —$C(O)R^7$ wherein $R^7$ is alkyl or —$(CH_2)_m$-cycloalkyl.

Yet another preferred embodiment of the invention are compounds of Formula I wherein:

Y is —$NR^4R^5$ where $R^4$ and $R^5$ together with the nitrogen atom to which they attach is

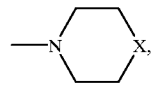

where $X=NR^6$ or O; and

Z is —$C(O)R^7$ wherein $R^7$ is aryl or aralkyl.

A preferred embodiment of the invention are compounds of Formula I wherein:

Y is —$NR^4R^5$; and

Z is —$C(O)CH(R^8)OC(O)NHR^3$.

Another preferred embodiment of the invention are compounds of Formula I wherein:

Y is —$NR^4R^5$ where $R^4$ is —$C(O)R^3$ and $R^5$ is $R^3$; and

Z is —$C(O)CH(R^8)OC(O)NHR^3$ wherein $R^8$ is alkyl.

A further preferred embodiment of the invention are compounds of Formula I wherein:

Y is —$NR^4R^5$ where $R^4$ and $R^5$ together with the nitrogen to which they attach is

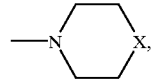

where $X=NR^6$ or O; and

Z is —$C(O)CH(R^8)OC(O)NHR^3$ wherein $R^8$ is alkyl.

A preferred embodiment of the invention are compounds of Formula I wherein:

Y is —$NR^4R^5$; and

Z is —$C(O)CH(R^8)NHC(O)R^3$.

Another embodiment of the invention are compounds of Formula I wherein:

Y is —$NR^4R^5$ where $R^4$ is —$C(O)R^3$ and $R^5$ is alkyl or aralkyl; and

Z is —$C(O)CH(R^8)NHC(O)R^3$ wherein $R^8$ is alkyl.

A further preferred embodiment of the invention are compounds of Formula I wherein:

Y is —$NR^4R^5$ where $R^4$ and $R^5$ together with the nitrogen atom to which they attach is

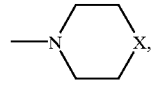

where $X=NR^6$ or O; and

Z is —$C(O)CH(R^8)NHC(O)R^3$ wherein $R^8$ is alkyl.

Methods of Synthesis

The compound of the present invention may be prepared according to the following methods. In carrying out the syntheses, one typically begins with a quantity of solid support that will provide enough compound after cleavage from the solid support for biological testing in the herein described assays. In the case where the solid support is TentaGel™, it is recommended that approximately 1 g of beads of about 180 microns in diameter, with a loading capacity of about 300 picoM per bead, be used. As the chemical yield of compounds after photolysis typically ranges from approximately 20% up to 60%, this quantity will provide a yield (approximately>10 mg) sufficient for biological testing in the given protease assays. For actual synthesis, the appropriate reagents and reaction conditions are applied to a reaction vessel containing the specified quantity of beads. During the syntheses, the beads or any suitable solid support may be washed free of any excess reagents or by-products before proceeding to the next step.

Optical Isomers—Diastereomers—Geometric Isomers

Some of the compounds described herein contain one or more asymmetric centers and may thus give rise to enantiomers, diastereomiers and other stereoisomeric forms which may be defined in terms of absolute stereochemistry as (R) or (S) or as (D) or (L) for amino acids. The present invention is meant to include all such possible diastereomers as well as their racemic and optically pure forms. Optically active (R) and (S) or (D) and (L) isomers may be prepared using chiral synthons or chiral reagents or resolved using conventional techniques. When the compounds described herein contain olefinic double bonds or other centers of geometric asymmetry, and unless specified otherwise, it is intended to include both E and Z geometric isomers. Likewise, all tautomeric forms are intended to be included.

A. Synthesis of Hydroxypropylamides.

A batch of amino-functionalized PEG-grafted polystyrene beads such as TentaGel 1 is used in the synthesis. It is first treated with bis-Fmoc lysine to increase the loading capacity of the resin. The Fmoc groups are removed using piperidine under standard conditions to which is then added 4-bromomethyl-3-nitrobenzoic acid 2. This is accomplished by the following method: The amine resin is suspended in DMF and treated with a solution of 2, HOBt and DIC in DMF. The suspension is shaken overnight, then drained and the resin is washed with DCM. The resin 3 is dried overnight under vacuum.

Resin 3 is reacted with a unique amino-TBS ether to generate compound 4. The coupling of each amine occurs through displacement of the linker bromide and formation of a new carbon-nitrogen bond. Two cycles of reactions are performed to ensure complete conversion. In the first cycle, the amine is added to a suspension of resin 3 in THF and the mixture is shaken overnight. The mixture is drained and the resin is washed with THF. The THF solution containing the excess amine is then concentrated, taken up in DCM, washed with aqueous sodium bicarbonate, dried over sodium sulfate and concentrated. The residue is taken up in DMF and reacted with the same resin for the second reaction cycle. Lithium iodide is added to the suspension and the mixture is shaken overnight. The suspension is drained and the resin is washed with DMF, methanol, DCM and dried overnight under vacuum to give resin 4. After coupling, a small portion of each batch of resin may be removed and titrated with picric acid to determine the extent of amine loading as a quality control for the reaction in this step.

The amine 4 is acylated by using acid chlorides. An acid chloride is added to a suspension of amine resin 4 in pyridine. The mixture is shaken overnight, drained and the resin is washed with DMF, methanol and DCM to give resin 5. Amine 4 reacts with acid chloride 6 to provide resin 7. The chloroacetoxy group is removed from the resin 7 by treatment with hydrazine in methanol for one hour at room temperature, drained and washed with DCM and acetonitrile. The resin 8, so obtained and shaken overnight, is then reacted with an isocyanate in acetonitrile in the presence of a base. The resin is finally drained and is washed with DMF, methanol and DCM. This gives the carbamate derivatized resin 9.

Either resin 5 or 9 is converted to the corresponding aldehyde resin 10 by acid deprotection and oxidation. Resin 5 or 9 is treated with dilute hydrochloric acid in methanol for five to eight hours to remove the t-butyldimethylsilyl (TBS) protecting group. The resin is then washed with DMF, methanol and DCM. The resulting alcohols are oxidized to the corresponding aldehydes by the following method: To a suspension of the resin in DMSO is added IBX and the mixture is shaken overnight. The suspension is drained and the resin is washed with DMSO then treated with another solution of IBX in DMSO for four hours. The mixture is then drained and the resin is washed with DMSO, methanol and DCM and dried overnight in vacuo to give the aldehydes 10 (Scheme 1).

The resin 10 can then be converted to homoallyl alcohol 11a by one of the following two methods: 1) The resin 10 is suspended in a mixture of THF and water, then allyl bromide and indium are added. After sonicating for up to 7.5 hours, the resin is drained and washed with water, THF and DCM to give alcohol resin 11a. 2) The resin 10 is suspended in DCM and treated with 2-allyl-4,4,5,5-tetramethyl-1,3,2-dioxaborolane. Following 16 hours of shaking, the resin is drained and washed with DCM and MeOH to give alcohol resin 11a.

Alcohol 11a is protected as its TBS ether by reaction of 11a with TBS trifluoromethanesulfonate (TBS-OTf) and 2,6-lutidine in DCM to give 11b. The double bond in 11b is oxidized to diol 12 using a catalytic amount of osmium tetroxide in acetone/water with NMO as the oxidant. The diol 12, so produced, is cleaved with sodium periodate in water to yield the aldehyde resin 13. This, in turn, is subjected to reductive amination with a primary or secondary amine, giving resin 14 or 15. In the case of resin 14, the amine is further reacted with either acetic anhydride or methanesulfonyl chloride in DCM in the presence of a base, e.g., DIEA. This derivatization yields resin 16 or 17.

Alternatively, resin 13 is reduced to the corresponding alcohol resin 18 using lithium borohydride. This resin 18 is reacted with an isocyanate in the presence of a catalytic amount of DBU in acetonitrile to provide the carbamate resin 19.

Resins 15,16,17 or 19 can be treated with dilute hydrochloric acid in methanol for five to eight hours to remove the t-butyldimethylsilyl (TBS) protecting group. The solid support is then washed with methanol and DCM to give resins 20–23.

Amides of Formula I (i.e., compounds 24–26 or 27) may be cleaved from resin compounds 20–23 by exposing them to UV light (ca. 360 nM) for 15–180 minutes at 25–50° C. in a suitable solvent such as methanol, methanol/water, ethanol, ethanol/water or a lower alkyl alcohol/water/trifluoracetic acid mixture (Scheme 2).

The following specific preparations of hydroxypropyl amides are examples of the present invention. Other specific examples can be found in Table I.

EXAMPLE 1

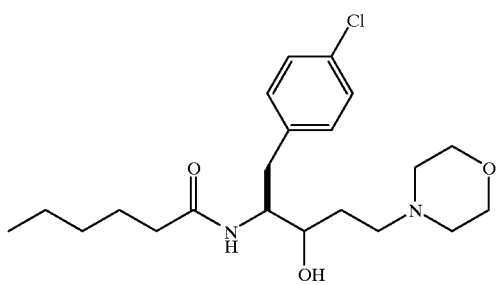

ENTRY 17, TABLE 1

Tentagel resin (S—NH$_2$, 1.2 g, 0.32 mmol/g, 0.384 mmol, 180–220 μm) was suspended in a solution of bis-Fmoc lysine (1.12 mmol, 0.68 g), and HOBt (1.12 mmol, 0.15 g), then treated with DIC (2.2 mmol, 0.36 mL). The suspension was shaken overnight, then drained and washed with DMF (3×15 mL), MeOH (3×15 mL) and DCM (3×15 mL).

A suspension of the Fmoc resin (1.2 g) in 1:1 piperidine-DMF was shaken for 1.5 hours, then drained and washed with DMF (3×15 mL), MeOH (3×15 mL) and DCM (3×15 mL). This resin was suspended in DMF (4 mL) and treated with a pre-incubated (one hour) solution of 4-bromomiethyl-3-nitro benzoic acid (2.2 mmol, 0.58 g), HOBt (2.3 mmol, 0.3 g) and DIC (4.5 mmol, 1 mL) in DMF (6 mL). The suspension was shaken overnight, then drained and washed with DMF (3×15 mL), methanol (3×15 mL) and DCM (3×15 mL).

The suspension of the resin (1 g) in THF (10 mL) was treated with t-butyldimethylsilyl-4-chlorophenylalaninol (1 mmol), and shaken overnight. The resin was then drained and washed with THF (3×15 mL). The filtrate was concentrated and the residue was taken up in DCM (20 mL) then washed with saturated aqueous sodium bicarbonate (20 mL). The aqueous phase was extracted with DCM (20 mL) and the combined organic phase was dried over sodium sulfate and concentrated in vacuo. The residue was then added to a suspension of the same resin in DMF (10 mL) along with lithium iodide (1.5 mmol, 0.2 g). The mixture was shaken for 24 hours, drained and the resin was washed with DMF (3×15 mL), MeOH (3×15 mL) and DCM (3×15 mL). The resin 4 was filtered and dried overnight in vacuo.

The suspension of resin 4 (1 g) in pyridine (5 mL)/DCM (5 mL) was treated with hexanoyl chloride (6 mmol). This suspension was shaken overnight, then drained and the resin was washed with DMF (3×10 mL), MeOH (3×10 mL) and DCM (3×10 mL).

The resin 5 (1 g) was suspended in a 1% solution (by volume) of concentrated HCl in methanol (15 mL). The resin mixture was shaken for seven hours, drained and washed with methanol (4×15 mL) and DCM (4×15 mL).

The resin (1 g) was suspended in DMSO (10 mL) and IBX (4.5 mmol) was added. The mixture was shaken overnight, drained and was washed with DMSO (2×15 mL). The resin was then suspended in DMSO and charged with another portion of IBX (4.5 mmol). The mixture was shaken for four hours, drained and the resulting resin was washed with DMSO (3×15 mL), methanol (3×15 mL) and DCM (3×15 mL). The resin was dried overnight in vacuo to provide resin 10.

The resin 10 (1 g) was suspended in a mixture of THF (20 mL) and water (20 mL). Indium powder (4.4 mmol) and allyl bromide (7 mmol) were then added and the mixture was sonicated for 5.5 hours. The resin was drained and washed with water (20 mL), THF (3×20 mL) and DCM (3×20 mL,) to give alcohol resin 11a.

Alcohol 11a (1 g) was suspended in DCM (25 mL) stirred with tert-buyldimethylsilyl trifluoromethanesulfonate (2.6 mmol) and 2,6-lutidine (3.4 mmol) at 0° C. for 5 minutes, then allowed to warm to room temperature as it was stirred for an additional 1.5 hours. The resin was then isolated by filtration and washed with MeOH (3×20 mL) and DCM (3×20 mL) to give the protected alcohol 11b.

Resin 11b (1 g) was suspended in a mixture of acetone (5 mL) and water (5 mL) and charged with NMO (2.5 mmol) and a catalytic amount of OsO$_4$ (20 mol %). The mixture was shaken overnight, drained and washed with water (3×15 mL), DMF (3×15 mL), methanol (3×15 mL) and DCM (3×15 mL) to provide the diol resin 12.

Diol resin 12 (1 g) was treated with four five minute cycles of saturated aqueous sodium periodate in water (10 mL). The resin was then washed with water (3×15 mL), methanol (3×15 mL), DCM (3×15 mL) and TMOF (15 mL) to furnish resin 13. The resin 13 was then suspended in TMOF and morpholine (17 mmol) was added. Following 30 minutes of shaking, the resin was drained and washed with 5% (v/v) AcOH/MeOH (3×15 mL), then suspended in 5% (v/v) AcOH/MeOH and reacted with NaBH$_3$CN (12 mmol). Following 15 hours of shaking, the resin 15 was drained and washed with 5% (v/v) AcOH/MeOH (3×15 mL), MeOH (3×15 mL), water (2×15 mL), 10% K$_2$CO$_3$/water (15 mL), water (2×15 mL) and MeOH (3×15 mL).

The resin 15 (1 g) was then treated with 1% (v/v) HCl/MeOH (10 mL). After six hours, the resin was drained and washed with MeOH (4×15 mL) and DCM (4×15 mL) to give the desired resin 23.

The resin 23 was suspended in MeOH (20 mL) and the compound cleaved from the resin by heating the suspension to 50° C. and irradiating for 3–4 hr at 353 nm. The suspension was filtered and the MeOH removed to give the title compound as confirmed by mass spectroscopy (mass spectrum (fab): m/z=397.3(M+H$^+$).

EXAMPLE 2

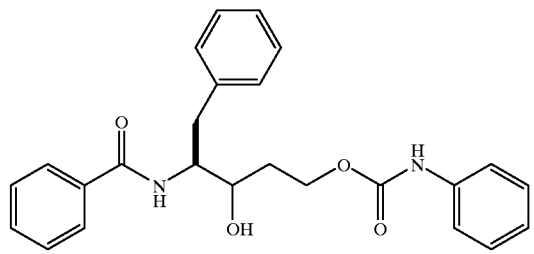

ENTRY 19, TABLE 1

Tentagel resin (S—NH$_2$, 1.2 g, 0.32 mmol/g, 0.384 mmol, 180–220 μm) was derivatized with bis-Fmoc lysine and then 4-bromomethyl-3-nitro benzoic acid as described in Example 1 above.

The suspension of the resin so obtained (1.2 g) in THF (30 mL) was treated with t-butyldimethylsilylphenylalaninol (0.5 g, 1 mmol), and shaken overnight. The resin was then drained and washed with THF (2×20 mL). The filtrate was concentrated, the residue was taken up in DCM (20 mL) and washed with saturated aqueous sodium bicarbonate (20 mL). The aqueous phase was extracted with DCM (20 mL) and the combined organic phase was dried over sodium sulfate and concentrated in vacuo. The residue was then added to a suspension of the same resin in DMF (10 mL) along with lithium iodide (0.7 mmol, 0.1 g). The mixture was shaken for 24 hours, drained and the resin was washed with DMF (20 mL), MeOH (3×20 mL) and $CH_2Cl_2$ (3×20 mL). The resin 4 was filtered and dried overnight in vacuo.

The suspension of resin 4 (1.67 g) in pyridine (10 mL) was treated with benzoyl chloride (14.8 mmol). This suspension was shaken overnight, then drained and washed with DMF (3×10 mL), MeOH (3×10 mL), DMF (3×10 mL) and $CH_2Cl_2$ (3×10 mL).

The resin (1 g) was then subjected to the same sequence of reactions including HCl hydrolysis, oxidation, addition of allyl bromide, silyl protection, osmylation, periodate cleavage as described in Example 1 above to yield resin 13.

Resin 13 (1 g) was treated with lithium borohydride (3 equiv) in THF for 30 minutes. The resin was drained and washed with DMF (3×15 mL), DCM (3×15 mL), MeOH (3×15 mL), water (3×15 mL), again with MeOH (3×15 mL) and then dried. The resin 18 (1 g) was suspended in acetonitrile (30 mL) to which was added phenylisocyanate (20 equiv) and DBU (0.1 mL). The resin mixture was shaken overnight and drained. The resin was washed with DMF (3×15 mL), DCM (3×15 mL), MeOH (3×15 mL), water (3×15 mL) and MeOH (3×15 mL). The resin 19 (1 g) was then treated with 1% (v/v) HCl/MeOH (10 mL). After six hours, the resin was drained and washed with MeOH (4×15 mL) and DCM (4×15 mL) to give the carbamate resin 22.

The resin 22 was suspended in MeOH (20 mL) and the compound cleaved from the resin by heating the suspension to 50° C. and irradiating for 3–4 hours at 353 nm. The suspension was filtered and the MeOH removed to give the title compound as confirmed by mass spectroscopy (mass spectrum (EI): mz=419.5(M+H$^+$).

EXAMPLE 3

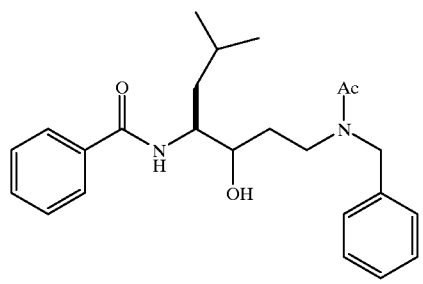

ENTRY 18, TABLE 1

Tentagel resin (S—NH$_2$, 1.2 g, 0.32 mmol/g, 0.384 mmol, 180–220 μm) was suspended in a solution of bis-Fmoc lysine (1.12 mmol, 0.68 g), and HOBt (1.12 mmol, 0.15 g), then treated with DIC (2.2 mmol, 0.36 mL). The suspension was shaken overnight, then drained and washed with DMF (3×15 mL), MeOH (3×15 mL) and DCM (3×15 mL).

A suspension of the Fmoc resin (1.2 g) in 1:1 piperidine-DMF was shaken for 1.5 hours, then drained and washed with DMF (3×15 ml), MeOH (3×15 mL) and DCM (3×15 mL). This resin was suspended in DMF (4 mL) and treated with a pre-incubated (one hour) solution of 4-bromomethyl-3-nitro benzoic acid (2.2 mmol, 0.58 g), HOBt (2.3 mmol, 0.3 g) DIC (4.5 mmol, 1 mL) in DMF (6 mL), The suspension was shaken overnight, then drained and washed with DMF (3×15 mL), methanol (3×15 mL) and DCM (3×15 mL).

The suspension of the resin 3 (1 g) in THF (10 mL) was treated with t-butyldimethylsilyl-4-leucinol (1 mmol) and shaken overnight. The resin was then drained and washed with THF (3×15 mL). The filtrate was concentrated and the residue was taken up in DCM (20 mL) then washed with saturated aqueous sodium bicarbonate (20 mL). The aqueous phase was extracted with DCM (20 mL) and the combined organic phase was dried over sodium sulfate and concentrated in vacuo. The residue was then added to a suspension of the same resin in DMF (10 mL) along with lithium iodide (1.5 mmol, 0.2 g). The mixture was shaken for 24 hours, drained and the resin was washed with DMF (3×15 mL), MeOH (3×15 mL), and DCM (3×15 mL). The resin 4 was filtered and dried overnight in vacuo.

The suspension of resin 4 (1 g) in pyridine (5 mL)/DCM (5 mL) was treated with benzoyl chloride (6 mmol). This suspension was shaken overnight, then drained and the resin was washed with DMF (3×10 mL), MeOH (3×10 mL) and DCM (3×10 mL).

The resin 5 (1 g) was suspended in a 1% solution (by volume) of concentrated HCl in methanol (15 mL). The mixture was shaken for seven hours, drained and the resin was washed with methanol (4×15 mL) and DCM (4×15 mL).

The resin (1 g) was suspended in DMSO (10 mL) and IBX (4.5 mmol) was added. The mixture was shaken overnight, drained and the resin was washed with DMSO (2×15 mL). The resin was then suspended in DMSO and charged with another portion of IBX (4.5 mmol). The mixture was shaken for four hours, drained and the resulting resin was washed with DMSO (3×15 mL), methanol (3×15 mL) and DCM (3×15 mL). The resin was dried overnight in vacuo to provide resin 10.

The resin 10 (1 g) was suspended in a mixture of THF (20 mL) and water (20 mL). Indium powder (4.4 mmol) and allyl bromide (7 mmol) were then added and the mixture was sonicated for 5.5 hours. The resin was drained and washed with water (20 mL), THF (3×20 mL) and DCM (3×20 mL) to give alcohol resin 11a.

Alcohol 11a (1 g) was suspended in DCM (25 mL) stirred with tert-buyldimethylsilyl trifluoromethanesulfonate (2.6 mmol) and 2,6-lutidine (3.4 mmol) at 0° C. for five minutes, then allowed to warm to room temperature as it stirred for an additional 1.5 hours. The resin was then isolated by filtration and washed with MeOH (3×20 mL) and DCM (3×20 mL) to give the protected alcohol 11b.

Resin 11b (1 g) was suspended in a mixture of acetone (5 mL) and water (5 mL) and charged with NMO (2.5 mmol) and a catalytic amount of OsO$_4$ (20 mol %). The mixture was shaken overnight, drained and washed with water (3×15 mL), DMF (3×15 mL), methanol (3×15 mL) and DCM (3×15 mL) to provide the diol resin 12.

Diol resin 12 (1 g) was treated with four five minute cycles of saturated aqueous sodium periodate (10 mL). The resin was then washed with water (3×15 mL), methanol (3×15 mL), DCM (3×15 mL) and TMOF (15 mL) to provide resin 13. The resin 13 was then suspended in TMOF and benzylamine (16 mmol) was added. Following 30 minutes of shaking, the resin was drained and washed with 5% (v/v) AcOH/MeOH (3×15 mL), then suspended in 5% (v/v) AcOH/MeOH and reacted with NaBH₃CN (12 mmol). Following 15 hours of shaking, the resin was drained and washed with 5% (v/v) AcOH/MeOH (3×15 mL), MeOH (3×15 mL), water (2×15 mL), 10% K₂CO₃/water (15 mL), water (2×15 mL) and MeOH (3×15 mL) to give resin 14.

Resin 14 (1 g) was treated with acetic anhydride (10 mmol), DMAP (0.1 mmol) and DIEA (6 mmol) in DCM (10 mL). After 18 hours of shaking, the resin was drained and washed with DMF (3×15 mL), methanol (3×15 mL) and DCM (3×15 mL) to provide resin 16.

The resin 16 (1 g) was then treated with 1% (v/v) HCl/MeOH (10 mL). After six hours, the resin was drained and washed with MeOH (4×15 mL) and DCM (4×15 mL) to give the desired resin 20.

The resin 20 was suspended in MeOH (20 mL) and the compound cleaved from the resin by heating the suspension to 50° C. and irradiating for 3–4 hr at 353 nm. The suspension was filtered and the MeOH removed to give the title compound as confirmed by mass spectroscopy (mass spectrum (fab):m/z=397.2(M+H⁺).

EXAMPLE 4

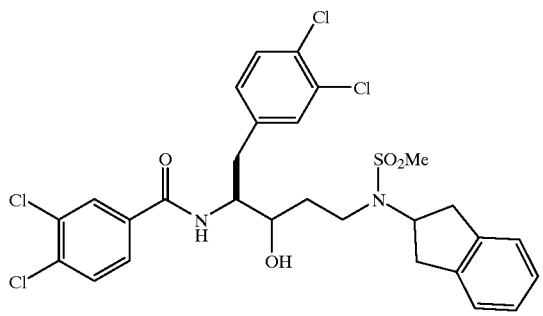

ENTRY 20, TABLE 1

Tentagel resin (S—NH₂, 1.2 g, 0.32 mmol/g, 0.384 mmol, 180–220 μm) is derivatized with bis-Fmoc lysine and then 4-bromomethyl-3-nitrobenzoic acid as described in Example 1 above.

The suspension of the resin so obtained (1.2 g) in THF (30 mL) is treated with t-butyldimethylsilyl-3,4-dichlorophenylalaninol (0.5 g, 1 mmol), and shaken overnight. The resin is then drained and washed with THF (2×20 mL). The filtrate is concentrated, the residue is taken up in DCM (20 mL) and washed with saturated aqueous sodium bicarbonate (20 mL). The aqueous phase is extracted with DCM (20 mL) and the combined organic phase is dried over sodium sulfate and concentrated in vacuo. The residue is then added to a suspension of the same resin in DMF (10 mL) along with lithium iodide (0.7 mmol, 0.1 g). The mixture is shaken for 24 hours, drained and the resin is washed with DMF (20 mL), MeOH (32 mL) and CH₂C₂ (3×20 mL). The resin 4 is filtered and dried overnight in vacuo.

The suspension of resin 4 (1.67 g) in pyridine (10 mL) is treated with 3,4-dichlorobenzoyl chloride (14.8 mmol). This suspension is shaken overnight, then drained and washed with DMF (3×10 mL), MeOH (3×10 mL), DMF (3×10 mL), and CH₂Cl₂ (3×10 mL).

The resin (1 g) was then subjected to HCl hydrolysis and oxidation as described in Example 3 above to yield resin 10. Aldehyde 10 is suspended in DCM and treated with 2-allyl-4,4,5,5-tetramethyl-1,3,2-dioxabomolane. Following 16 hours of shaking, the resin is drained and washed with DCM and MeOH to give alcohol 11a. Resin 11a is subjected to silyl protection, osmylation, periodate cleavage and reductive amination, using 2-aminoindane as the amine component, as described in Example 3 above to yield resin 14.

Resin 14 (1 g) is treated with methanesulfonyl chloride (20 equiv) in pyridine for 3 hours. The resin is drained and washed with DMF (3×15 mL), DCM (3×15 mL), MeOH (3×15 mL), water (3×15 mL), again with MeOH (3×15 mL) and then dried. The resin 17 (1 g) is then treated with 1% (v/v) HCl/MeOH (10 mL). After six hours, the resin is drained and washed with MeOH (4×15 mL) and DCM (4×15 mL) to give the sulfonamide resin 21.

The resin 21 is suspended in MeOH (20 mL) and the compound cleaved from the resin by heating the suspension to 50° C. and irradiating for 3–4 hr at 353 nm. The suspension is filtered and the MeOH removed to give the title compound.

EXAMPLE 5

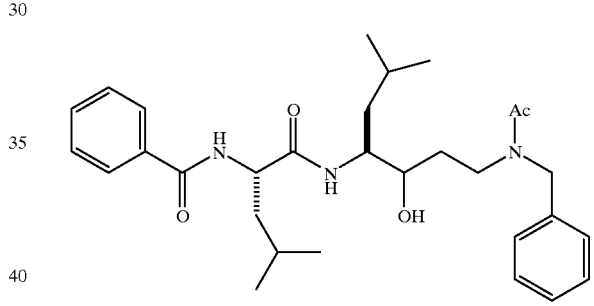

Tentagel resin (S—NH₂, 1.2 g, 0.32 mmol/g, 0.384 mmol, 180–220 μm) is derivatized with bis-Fmoc lysine and then 4-bromomethyl-3-nitrobenzoic acid and t-butyldimethylsilyl-leucinol as described in Example 1 above.

The suspension of resin 4 (1.67 g) in pyridine (10 mL) is treated with N-benzoyl leucinyl fluoride (14.8 mmol). This suspension is shaken overnight, then drained and washed with DMF (3×10 mL), MeOH (3×10 mL), DMF (3×10 mL) and CH₂Cl₂ (3×10 mL).

The resin (1 g) is then subjected to the same sequence of reactions including HCl hydrolysis, oxidation, addition of allyl bromide, silyl protection, osmylation, periodate cleavage, reductive amination using benzylamine, acetylation, acid-catalyzed removal silyl protecting group as described in Example 3 above to yield resin 20.

The resin 20 is suspended in MeOH (20 mL) and the compound cleaved from the resin by heating the suspension to 50° C. and irradiating for 3–4 hr at 353 nm. The suspension is filtered and the MeOH removed to give the title compound.

Using these methods, compounds in Table 1 were prepared. The compounds in Table 1 typically inhibit either plasmepsin or cathepsin D at a concentration ($IC_{50}$) of less than 350 micromolar.

Utility of the Compounds of the Invention

The compounds of the present invention, alone or in combination with other pharmaceutical agents, are therefore useful in treating humans, by inhibiting the action of plasmepsin or the action of cathepsin D. Such conditions include, but are not limited to the following:

Malaria (Francis, S. E., Gluzman, I. Y., Oksman, A., Knickerbocker, A., Mueller, R., Bryant, M. L., Sherman, D. R., Russell, D. G. and Goldberg, D. E. (1994) *EMBO J*, 13, 306–317); muscular distrophy (Gopalan, P., DuFrense, M. J. and Warner, A. H. (1996) *Can. J. Physiol. Pharmacol.*, 65, 124–129); breast cancer (Westley, B., May, F. (1996) *Eur. J. Cancer*, 32A, 15–24); and Alzheimer's disease (Dreyer, R. N., Bausch, K. M., Fracasso, P., Hammond, L. J., Wunderlich, D., Wirak, D. O., Davis, G., Brini, C. M., Bucholz, T. M., Konig, G., Kamark, M. E., and Tamburini, P. P. (1994) *Eur. J. Biochem.*, 224, 265–271 and Ladror, U.S., Synder, S. W., Wang, G. T., Holzman, T. F., and Krafft, G. A. (1994) *J. Biol. Chem.*, 269, 18422–18428).

The inhibitory activity of the compounds in the present invention can be assessed using the appropriate assay systems specific for plasmepsin or cathepsin D activity.

Assays for Determining Biological Activity

Materials

Plasmepsin II was obtained from Daniel E. Goldberg, Washington University. The plasmepsin II substrate, (DABCYL)-γ-aminobutyric acid-Glu-Arg-Met-Phe-Leu-Ser-Phe-Pro-EDANS, and the cathepsin D substrate, DABCYL-γ-aminobutyric acid-Lys-Pro-Ile-Glu-Phe-Phe-Arg-Leu-EDANS were purchased as a custom synthesis product from AnaSpec. Inc., 2149 O'Toole Avenue, Suite F, San Jose, Calif. 95131.

Cathepsin D from human liver was purchased from ART Biochemicals, Athens Research Technology, PO Box 5494, Athens, Ga. 30604.

Method for Plasmepsin II

The assay mix contained 50 mM sodium acetate (pH 5.0), 1 mg/ml BSA, 0.01% Tween 20, 12.5% glycerol, 18% DMSO and 12 μM plasmepsin substrate. Twenty five μL of the assay mix was added to each well of the 96-well microtiter plate containing dried down bead eluate or empty control wells. The plates were then sonicated and mixed. Then 25 μL of 8 nM plasmepsin II in a mixture of 50 mM sodium acetate (pH 5.0), 1 mg/ml BSA, 0.01% Tween 20, and 12.5% glycerol was added to the assay mix. The final concentrations were: 4 nM plasmepsin II, 6 μM plasmepsin substrate, 9% DMSO, 50 mM sodium acetate (pH 5.0), 1 mg/ml BSA, 0.01% Tween 20 and 12.5% glycerol. The reaction was incubated for 10 minutes at 25° C. and then quenched by the addition of 25 μL of 1 M Tris (pH 8.5) and 50% DMSO to achieve a final concentration of 0.33 M Tris and 23% DMSO. The EDANS fluorescence was measured using the Tecan, SLT FluoStar fluorescence plate reader with an excitation filter of 350 nm and an emission filter 510 nm. The background was determined by 25 μL of 50 mM sodium acetate (pH 5.0), 1 mg/ml BSA, 0.01% Tween 20, and 12.5% glycerol without enzyme.

Method for Cathepsin D

The assay mix contained 25 mM sodium formate (pH 3.5), 1 mg/ml BSA, 12% DMSO and 12 μM cathepsin D substrate. Twenty five μL of the assay mix was added to each well of the 96-well microtiter plate containing dried down bead eluate or empty control wells. The plates were then sonicated and mixed. Then 25 μL of 1.6 nM cathepsin D in a mixture of 25 mM sodium formate (pH 3.5) and 1 mg/ml BSA, was added to the assay mix. The final concentrations were: 0.8 nM cathepsin D, 6 μM cathepsin D substrate, 6% DMSO, 25 mM sodium formate (pH 3.5), and 1 mg/ml BSA. The reaction was incubated for 10 minutes at 25° C. and then quenched by the addition of 25 μL of 1 M Tris (pH 8.5) and 50% DMSO to achieve a final concentration of 0.33 M Tris and 21% DMSO. The EDANS fluorescence was measured as stated above. The background was determined by 25 μL of 50 mM sodium formate (pH 3.5), and 1 mg/ml BSA without enzyme.

Pharmaceutical Compositions—Administration

Any suitable route of administration may be employed for providing a patient with an effective dosage of compounds of the invention. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise the inventive hydroxypropyl amides as the active ingredients, and may also contain a pharmaceutically acceptable carrier, and optionally, other therapeutic ingredients. Carriers such as starches, sugars, microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. Methods for their preparation are well known in the art.

Because of their ease of administration, tablets and capsules represent the most advantageous oral dosage unit forms, in which case solid pharmaceutical carriers are employed. If desired, tablets may be coated by standard aqueous or nonaqueous techniques. In addition to the common dosage forms set out above, the compounds of the present invention may also be administered by controlled or sustained release means and delivery devices.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods or pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

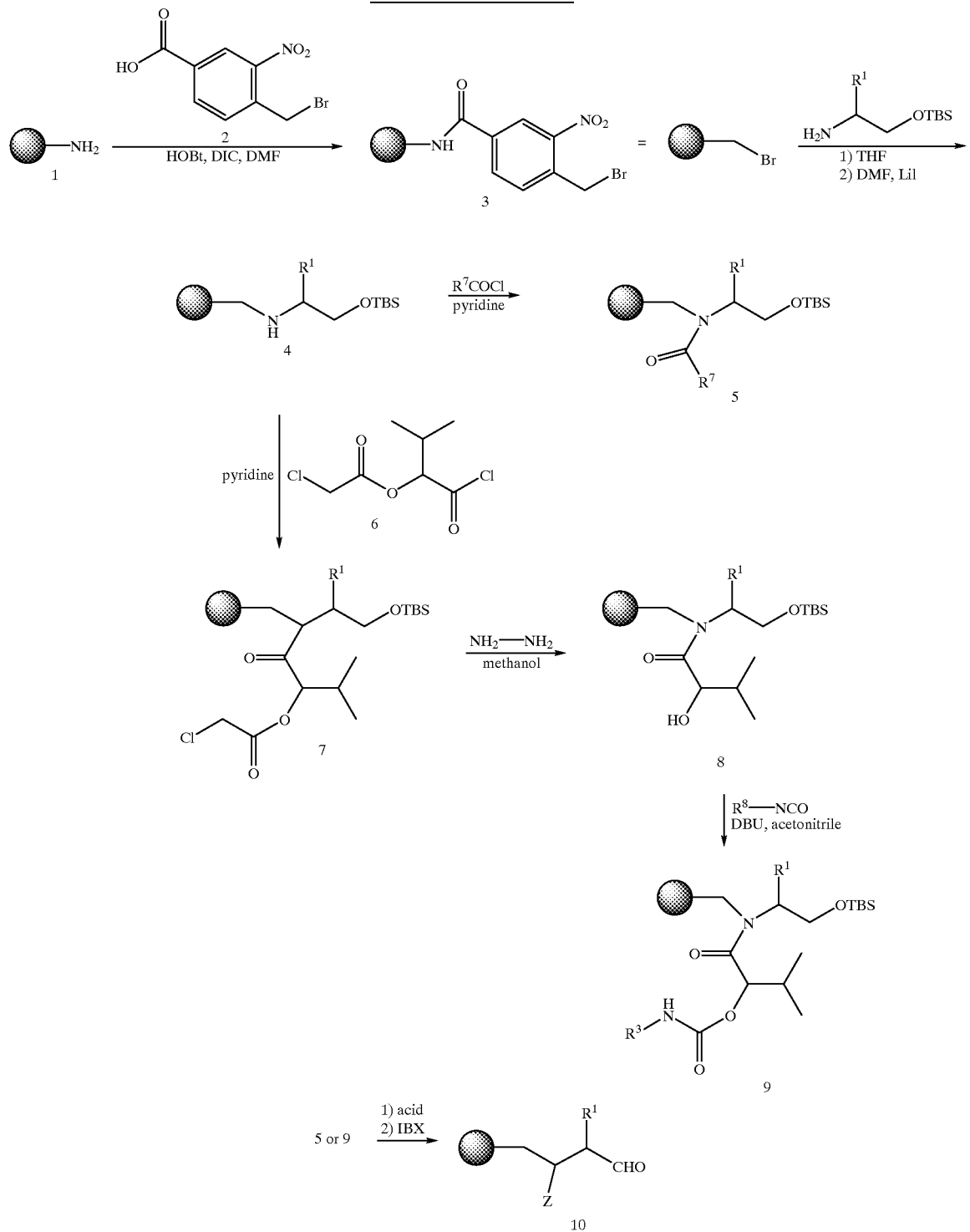
Scheme 1.
Hydroxypropylamide synthesis.

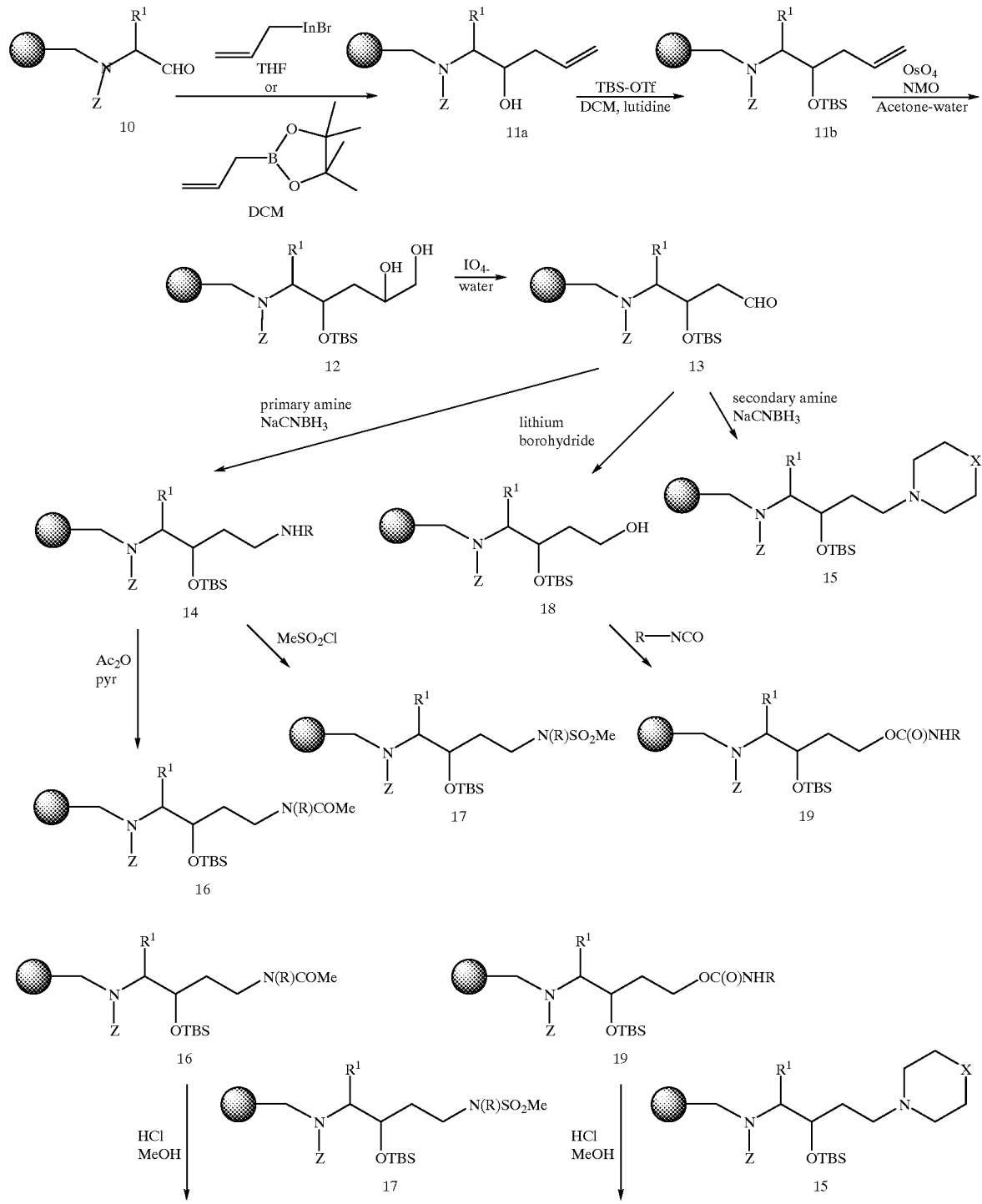
Scheme 2.
Hydroxypropylamide synthesis.

-continued
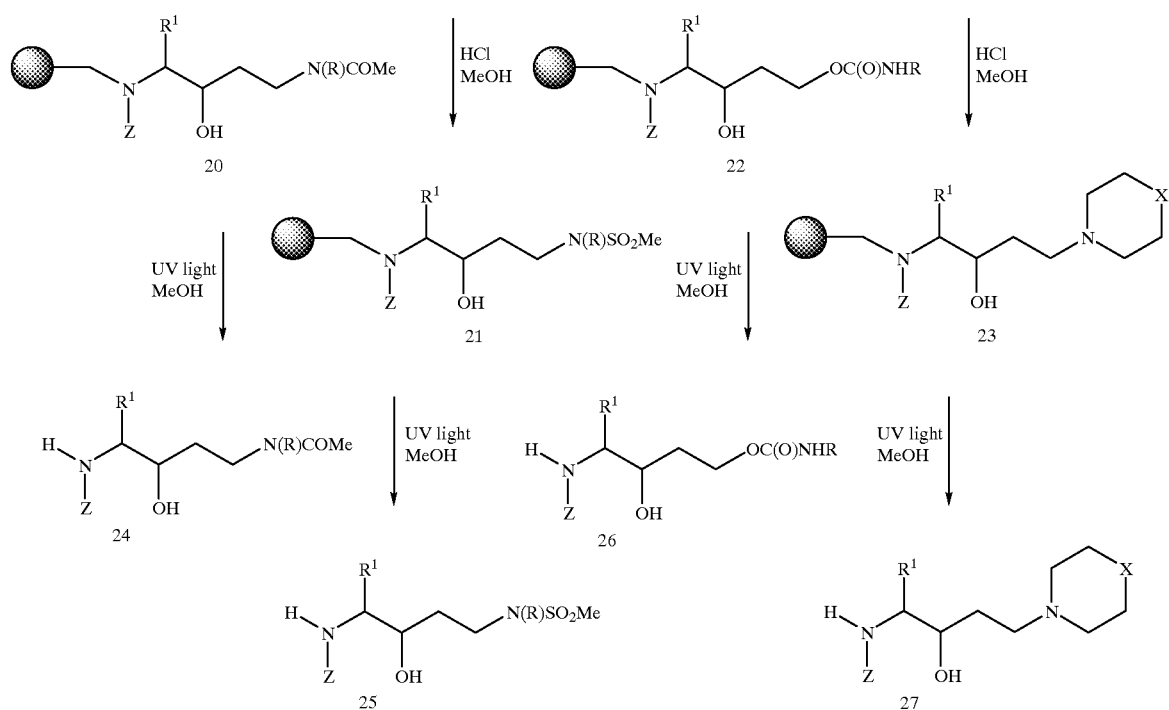
TABLE 1
Hydroxypropylamides.
Entry Structure
1
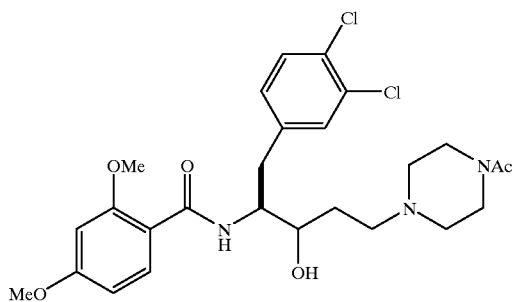
2
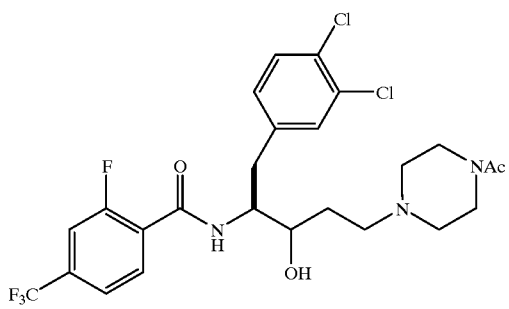

TABLE 1-continued
Hydroxypropylamides.
Entry Structure
3 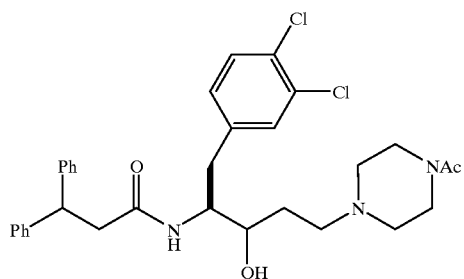
4 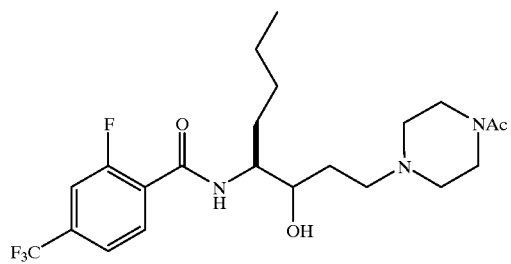
5 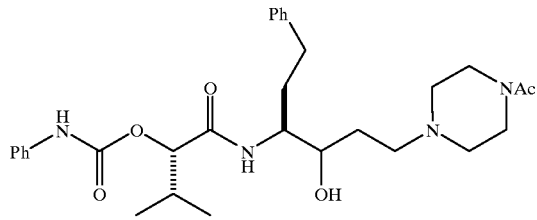
6 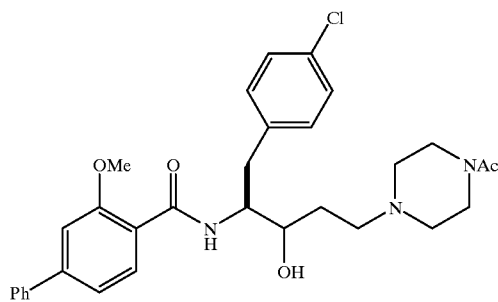
7 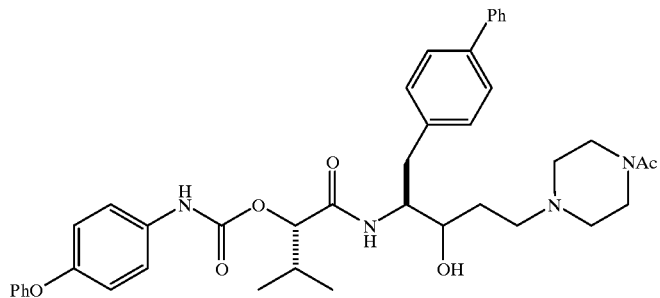

TABLE 1-continued
Hydroxypropylamides.
Entry Structure
8
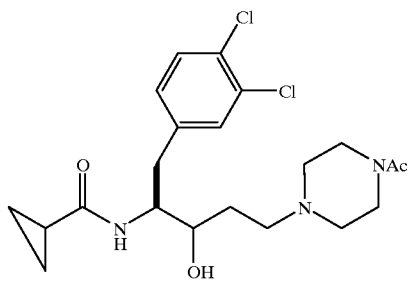
9
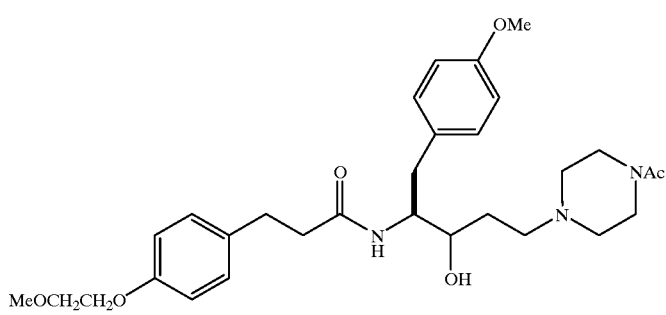
10
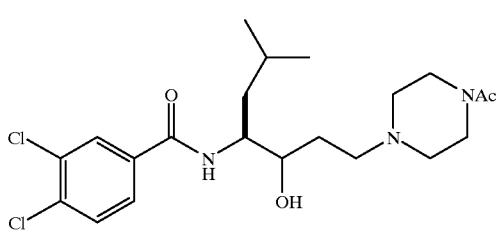
11
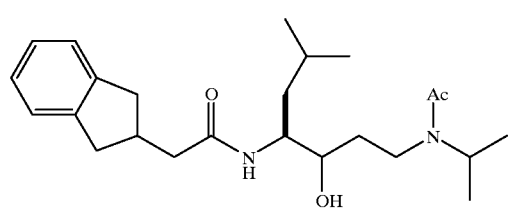
12
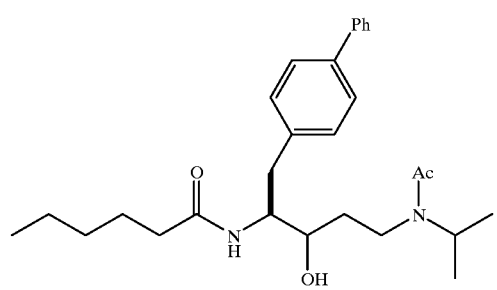

TABLE 1-continued
Hydroxypropylamides.
Entry Structure
13
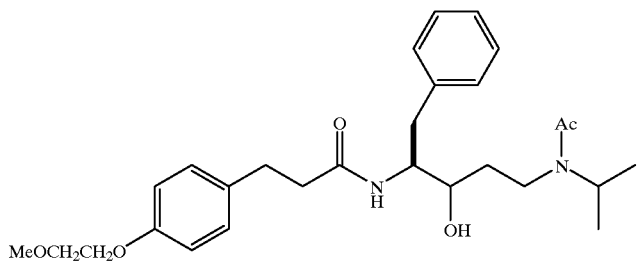
14
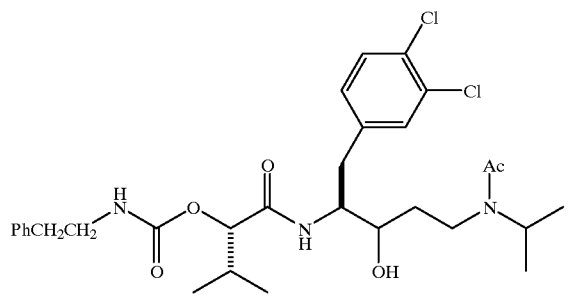
15
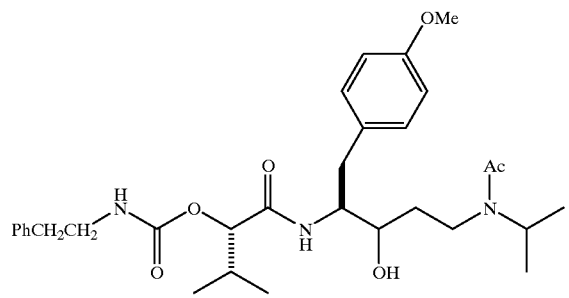
16
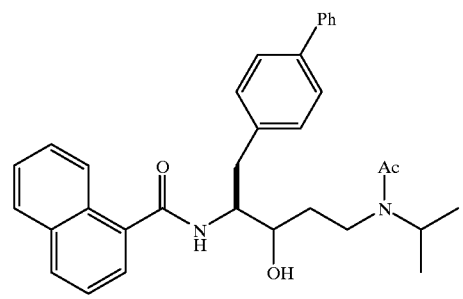
17
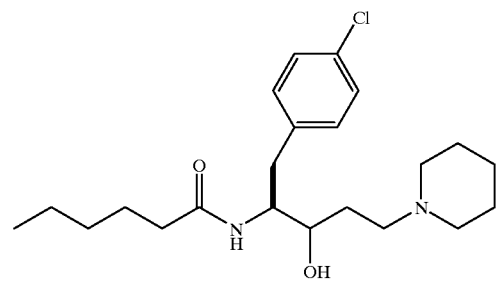

TABLE 1-continued
Hydroxypropylamides.
| Entry | Structure |
|---|---|
| 18 | 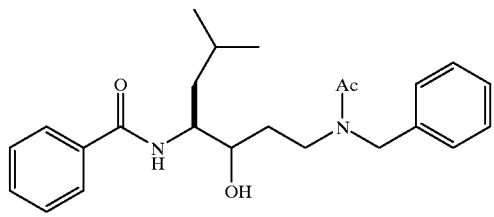 |
| 19 | 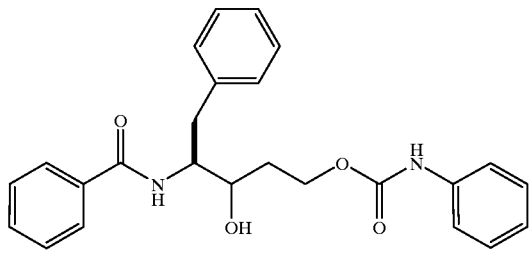 |
| 20 | 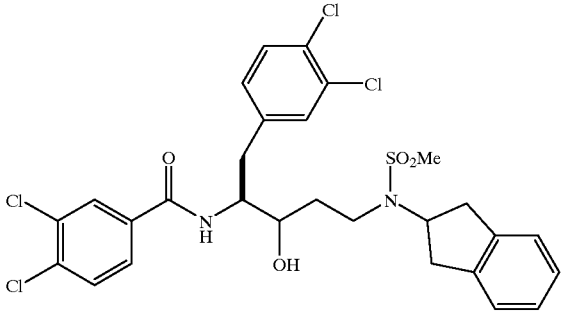 |
| 21 | 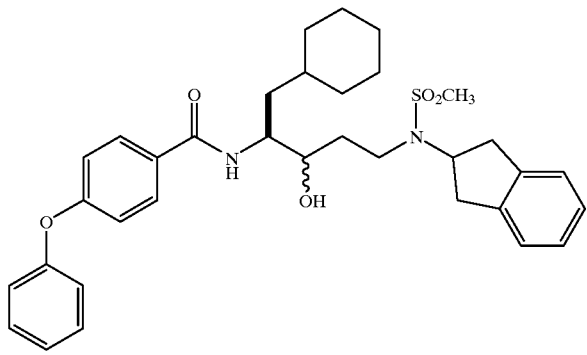 |
| 22 | 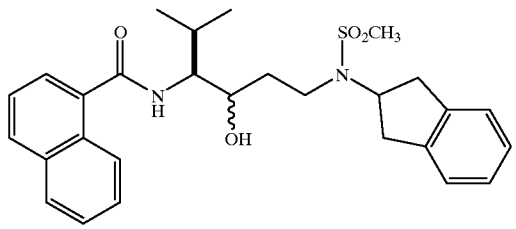 |

TABLE 1-continued
Hydroxypropylamides.
Entry Structure
23
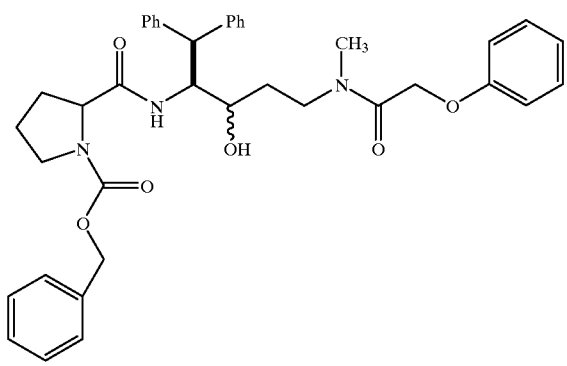
24
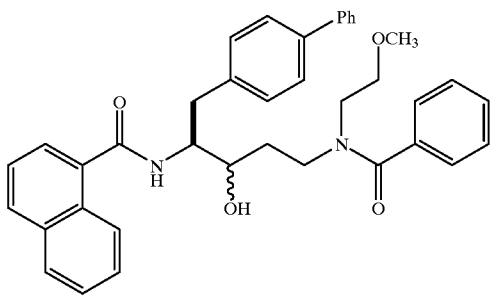
25
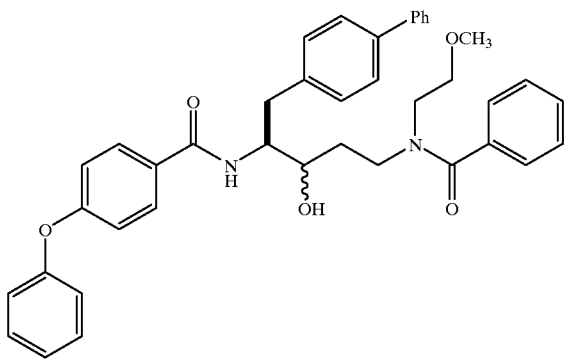
26
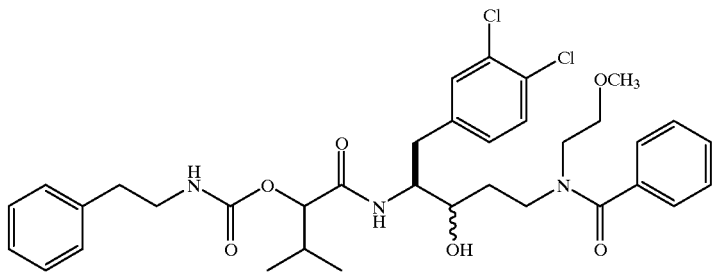

TABLE 1-continued

Hydroxypropylamides.

| Entry | Structure |
|---|---|
| 27 | 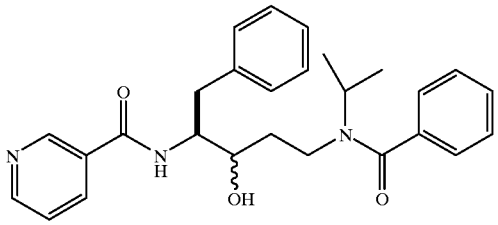 |

We claim:

1. A compound of Formula I:

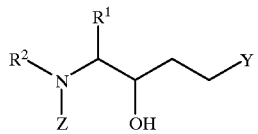

wherein:
R¹ is aralkyl,
R² is H;
R³ is alkyl, aralkyl, aryl or aryloxyalkyl;
Y is —NR⁴R⁵, wherein R⁴ and R⁵ together with the nitrogen atom to which they attach is

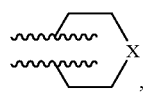

where X=NR⁶ or O;
R⁶ is chosen from the group consisting of H, R³, —C(O)R³ and —SO₂R³;
Z is chosen from the group consisting of —C(O)R⁷, —C(O)CH(R⁸)OC(O)NHR³; and —C(O)CH(R⁸)NHC(O)R³ wherein
R⁷ is chosen from the group consisting of alkyl, aralkyl, aryl, —(CH₂)ₘ-cycloalkyl, heteroaryl,

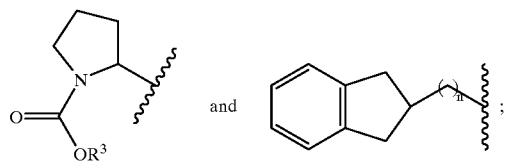

and
R⁸ is chosen from the group consisting of H, alkyl, aralkyl and —(CH₂)ₘ-cycloalkyl.

2. The compound of claim 1 wherein:
R² is H.

3. The compound of claim 2 wherein:
Y is —NR⁴R⁵; and
Z is —C(O)R⁷.

4. The compound of claim 3 wherein:
Y is

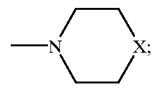

and
R⁷ is alkyl, aralkyl, aryl or —(CH₂)ₘ-cycloalkyl.

5. The compound of claim 4 wherein:
R⁷ is alkyl or —(CH₂)ₘ-cycloalkyl.

6. The compound of claim 4 wherein:
R⁷ is aryl or aralkyl.

7. The compound of claim 2 wherein:
Y is —NR⁴R⁵; and
Z is —C(O)CH(R⁸)OC(O)NHR³.

8. The compound of claim 7 wherein:
Y is

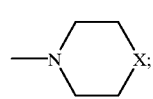

and
R⁸ is alkyl.

9. The compound of claim 2 wherein:
Y is —NR⁴R⁵; and
Z is —C(O)CH(R⁸)NHC(O)R³.

10. The compound of claim 9 wherein:
Y is

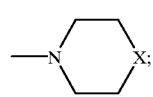

and
R⁸ is alkyl.

* * * * *